US010265250B2

(12) United States Patent
Doering et al.

(10) Patent No.: US 10,265,250 B2
(45) Date of Patent: Apr. 23, 2019

(54) ANTIPERSPIRANT AEROSOL COMPOSITIONS HAVING REDUCED RESIDUE BUILD-UP

(71) Applicant: Henkel AG & Co. KGaA, Duesseldorf (DE)

(72) Inventors: Thomas Doering, Dormagen (DE); Sandra Mausberg, Haan (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 15/345,975

(22) Filed: Nov. 8, 2016

(65) Prior Publication Data

US 2017/0135913 A1    May 18, 2017

(30) Foreign Application Priority Data

Nov. 17, 2015    (DE) .......................... 10 2015 222 647

(51) Int. Cl.

| | |
|---|---|
| *A61K 8/04* | (2006.01) |
| *A61K 8/26* | (2006.01) |
| *A61K 8/31* | (2006.01) |
| *A61K 8/37* | (2006.01) |
| *A61K 8/49* | (2006.01) |
| *A61K 8/58* | (2006.01) |
| *A61K 8/96* | (2006.01) |
| *A61Q 15/00* | (2006.01) |

(52) U.S. Cl.
CPC .............. *A61K 8/046* (2013.01); *A61K 8/26* (2013.01); *A61K 8/31* (2013.01); *A61K 8/37* (2013.01); *A61K 8/4973* (2013.01); *A61K 8/585* (2013.01); *A61K 8/965* (2013.01); *A61Q 15/00* (2013.01); *A61K 2800/22* (2013.01); *A61K 2800/262* (2013.01)

(58) Field of Classification Search
None
See application file for complete search history.

(56) References Cited

U.S. PATENT DOCUMENTS

| | | | | |
|---|---|---|---|---|
| 4,278,655 | A | * 7/1981 | Elmi | ........................ A61K 8/37 424/47 |
| 5,635,165 | A | * 6/1997 | Panitch | .................. A61K 8/042 424/400 |
| 5,945,085 | A | * 8/1999 | Salas | ...................... A61Q 15/00 424/45 |
| 2007/0036738 | A1 * | 2/2007 | Fletcher | ................. A61K 8/046 424/65 |

FOREIGN PATENT DOCUMENTS

| | | |
|---|---|---|
| DE | 68908955 T2 | 4/1994 |
| DE | 102015210478 A1 | 4/2016 |
| WO | 9118586 A1 | 12/1991 |

* cited by examiner

*Primary Examiner* — Susan T Tran
*Assistant Examiner* — William Craigo
(74) *Attorney, Agent, or Firm* — P. Scott Smith

(57) ABSTRACT

The present invention relates to antiperspirant cosmetic agents in the form of an aerosol, which comprise a combination of a specific aluminum salt with at least one non-volatile ester and at least one volatile silicone compound. The aforementioned combination results in reduced residue build-up and improved cosmetic properties, and in particular in an improved dryness sensation on the skin. These agents furthermore have an outstanding antiperspirant action. The present invention further relates to a method for preventing and/or reducing perspiration of the body, using the cosmetic agent according to the invention, and to the use of the aforementioned combination of propellant-containing cosmetic agents.

15 Claims, No Drawings

ANTIPERSPIRANT AEROSOL COMPOSITIONS HAVING REDUCED RESIDUE BUILD-UP

FIELD OF THE INVENTION

The present invention generally relates to propellant-containing antiperspirant cosmetic agents, which comprise a specific aluminum salt and at least one non-volatile ester and one volatile silicone compound in a certain weight ratio. The aforementioned antiperspirant agents have an outstanding antiperspirant action and reduced residue build-up, in particular on textiles.

The present invention further relates to a non-therapeutic cosmetic method for preventing and/or reducing perspiration of the body, in which the antiperspirant cosmetic agent according to the invention in the form of an aerosol is applied to the skin, and in particular to the skin of the axilla region, and remains there for at least 1 hour.

Finally, the present invention relates to the use of a combination made of a specific aluminum compound, at least one non-volatile ester, and at least one volatile silicone compound in propellant-containing cosmetic agents for improving the antiperspirant action, while also reducing residue build-up, in particular on textiles.

BACKGROUND OF THE INVENTION

Washing, cleaning, and caring for one's body is a basic human need, and modern industry is continually attempting to satisfy these needs of humans in a variety of ways. The lasting elimination, or at least reduction, of body odor and underarm perspiration is particularly important for daily hygiene. Numerous special deodorizing or antiperspirant body care agents are known in the related art, which were developed for use in body regions that have a high density of sweat glands, in particular in the axilla region. These are formulated in a wide variety of forms of application, for example as powders, in stick form, as aerosol sprays, pump sprays, liquid and gel-like roll-on applications, creams, gels, and as saturated flexible substrates (deodorant wipes).

Cosmetic antiperspirants of the related art include at least one antiperspirant salt. So as to achieve a high reduction in sweat, the use of aluminum-zirconium halides is preferred in the related art. The antiperspirant action of these salts can be further enhanced, for example, by thermal treatment and the addition of ligands or phosphates. These aforementioned highly effective salts, however, cannot be used in propellant-containing agents for inhalation toxicity reasons.

The less effective aluminum chlorohydrate is therefore used as the antiperspirant salt in propellant-containing agents. However, using aluminum chlorohydrate in amounts of more than 5.0 wt. %, based on the total weight of the agent, which are needed for good antiperspirant action, results in poor skin tolerability of these agents and the build-up of clearly visible, and therefore undesirable, residue on textiles.

A need therefore exists for propellant-containing antiperspirant cosmetic agents that exhibit a high antiperspirant action and reduced residue build-up, in particular on textiles.

It was therefore the object of the present invention to provide a propellant-containing antiperspirant cosmetic agent that prevents, or at least lessens, the drawbacks of the related art and has a high antiperspirant action and reduced residue build-up, in particular on textiles. Furthermore, these cosmetic agents should be cost-effective to produce, be storage-stable, and have good skin tolerability and good cosmetic properties.

Surprisingly, it has now been found that the use of a combination of non-volatile esters and volatile silicone compounds in certain weight ratios allows the amount of the aluminum salt to be decreased, without adversely affecting the antiperspirant action. Moreover, reduced residue build-up, in particular on textiles, is also achieved. Furthermore, the use of reduced amounts of the aluminum salt results in improved cosmetic properties, and in particular in an improved dryness sensation on the skin, and in improved skin tolerability.

Furthermore, other desirable features and characteristics of the present invention will become apparent from the subsequent detailed description of the invention and the appended claims, taken in conjunction with this background of the invention.

BRIEF SUMMARY OF THE INVENTION

An antiperspirant cosmetic agent, comprising, based on the total weight thereof, 2.5 to 15 wt. % of at least one aluminum salt of formula (I)

$$Al_a(OH)_bCl_c \tag{I},$$

where a denotes numbers from 1 to 4, b denotes numbers from 1 to 4.9, and c denotes numbers from 1.5 to 3; 3 to 15 wt. % of at least one non-volatile ester; at least one volatile silicone compound; and at least one propellant, wherein the weight ratio of the at least one non-volatile ester b) to the at least one volatile silicone compound c) in the agent is 10:1 to 1:1.5.

Use of a combination of aluminum salts of formula (I)

$$Al_a(OH)_bCl_c \tag{I},$$

where a denotes numbers from 1 to 4, b denotes numbers from 1 to 4.9, and c denotes numbers from 1.5 to 3; at least one non-volatile ester; and at least one volatile silicone compound in propellant-containing cosmetic agents for improving the antiperspirant action, while also reducing residue build-up, in particular on textiles.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

A subject matter of the present invention is an antiperspirant cosmetic agent, comprising, based on the total weight thereof,
a) 2.5 to 15 wt. % of at least one aluminum salt of formula (I)

$$Al_a(OH)_bCl_c \tag{I},$$

where
a denotes numbers from 1 to 4;
b denotes numbers from 1 to 4.9, and
c denotes numbers from 1.5 to 3;
b) 5.0 to 25 wt. % of at least one non-volatile ester;
c) at least one volatile silicone compound;
d) and at least one propellant, wherein the weight ratio of the at least one non-volatile ester b) to the at least one volatile silicone compound b) in the agent is 10:1 to 1:1.5.

According to the invention, the term "antiperspirant" shall be understood to mean the decrease or reduction of perspiration of the body's sweat glands.

Furthermore, the term "aluminum salt" shall be understood to mean a chemical compound that is composed of positively charged ions (also referred to as cations) in the form of aluminum, and negatively charged ions (also referred to as anions) in the form of halides, and in particular chlorides, and hydroxides. Ionic bonds exist between these ions. However, aside from aluminum, these aluminum salts do not contain any cations of another kind, and in particular no zirconium ions.

Furthermore, the term "esters" shall be understood to mean carboxylic acid derivatives comprising at least one functional group $R_1$—C(O)—O—$R_2$, wherein $R_1$ and $R_2$, each independently of one another, denote $C_2$ to $C_{30}$ alkyl groups, $C_2$ to $C_{30}$ alkylene groups, and $C_2$ to $C_{30}$ aralkyl groups. Preferred esters include exactly one of the aforementioned functional group. Such esters can be obtained, for example, by reacting a carboxylic acid with an alcohol. Non-volatile esters are understood to mean esters that have a vapor pressure of less than 2.66 Pa (0.02 mm Hg) at 20° C. and an ambient pressure of 1,013 hPa.

Moreover, the term "volatile silicone compounds" is understood to mean compounds that have a vapor pressure of 2.66 Pa to 40,000 Pa (0.02 to 300 mm Hg), especially of 10 to 12,000 Pa (0.1 to 90 mm Hg), further preferably of 13 to 3,000 Pa (0.1 to 23 mm Hg), and in particular of 15 to 500 Pa (0.1 to 4 mm Hg) at 20° C. and an ambient pressure of 1,013 hPa, and that comprise at least two silicon atoms linked via an oxygen atom.

Unless indicated otherwise, in the present invention the wt. % information refers to the total weight of the cosmetic agents according to the invention, wherein the sum of all ingredients of the agents according to the invention is 100 wt. %.

As a first essential component a), the antiperspirant cosmetic agent according to the invention comprises at least one aluminum salt of formula (I).

According to the invention, the antiperspirant cosmetic agents advantageously comprise aluminum salts in which the subscripts a, b, and c of formula (I) denote certain numbers. It is therefore preferred within the scope of the present invention if the agent comprises at least one aluminum salt of formula (Ia) $Al_d(OH)_eCl_f$, where d denotes the number 2, e denotes the number 4.5, and f denotes the number 1.5. Such aluminum salts therefore have the formula $Al_2(OH)_{4.5}Cl_{1.5}$ and are known by the name of aluminum sesquichlorohydrate. The use of aluminum sesquichlorohydrate, in combination with the non-volatile ester and the volatile silicone compound, has proven to be particularly advantageous with respect to the antiperspirant power and the reduced residue build-up.

It is preferred according to the invention if the antiperspirant cosmetic agent comprises aluminum salts of formula (I), and in particular of formula (Ia), having a certain molar ratio of aluminum to chloride. Preferred antiperspirant cosmetic agents are therefore characterized by comprising at least one aluminum salt of formula (I), and in particular an aluminum salt of formula (Ia), having a molar ratio of aluminum to chloride of 1.26:1 to 1.90:1, especially 1.35:1 to 1.88:1, preferably 1.40:1 to 1.88:1, and in particular 1.65:1 to 1.88:1. The use of aluminum salts of formula (I), and in particular of formula (Ia), having the aforementioned molar ratios of aluminum to chloride, has proven particularly advantageous with respect to the antiperspirant action, the reduced residue build-up, and the improved dryness sensation.

It may furthermore be preferred according to the invention if the aluminum salts of formula (I), and in particular of formula (Ia), that are used have a high chloride content. Preferred antiperspirant cosmetic agents are therefore characterized by comprising at least one aluminum salt of formula (I), and in particular of formula (Ia), having a chloride content of 5 to 35 wt. %, especially 10 to 30 wt. %, preferably 15 to 25 wt. %, and in particular 17 to 20 wt. %, based on the total weight of the aluminum salt of formula (I), and in particular of formula (Ia). The use of such salts results in a high antiperspirant action and in reduced residue build-up compared to aluminum salts having different, and in particular lower, chloride contents. The chloride content of the aluminum salts can be determined by way of potentiometric titration against a silver nitrate solution as the standard, for example.

It has been found to be advantageous within the scope of the present invention if the antiperspirant cosmetic agents comprise aluminum salts of formula (I), and in particular aluminum salts of formula (Ia), where d=2, e=4.5, and f=1.5, which are present in activated form and have a high content of polymeric aluminum complexes (hereafter also referred to as Al complexes) having a low molecular weight. These polymeric Al complexes are created by dissociation of the aluminum salts in ARM) aqua complexes and subsequent formation of polymeric Al complex with hydroxide and oxide bridges between the aluminum ions. Polymeric Al complexes having a high molecular weight, however, have a lower antiperspirant action than polymeric Al complexes having a low molecular weight.

The formation of polymeric Al complexes having low molecular weights can be determined by way of size exclusion chromatography, for example. For this purpose, a column is used that contains silanized porous silica microspheres having a particle size of 5 μm (for example Agilent Zorbax PSM 60S column, which is commercially available from Agilent). A suitable eluent is 0.02 M HCl. During the analysis of the aluminum salts of formula (I), and in particular of formula (Ia), used according to the invention, 5 to 6 peaks are obtained, which represent polymeric Al complexes having different molecular weight ranges. Peaks 1 and 2 represent polymeric Al complexes having an average molecular weight of 5,000 to 10,000 g/mol, peak 3 represents polymeric Al complexes having an average molecular weight of 2,000 to 4,000 g/mol, and peak 4 represents polymeric Al complexes having an average molecular weight of 500 to 1,500 g/mol. Finally, peaks 5 and 6 represent polymeric Al complexes having an average molecular weight of 135 to 270 g/mol.

The surface area of the respective peak is directly proportional to the amount of polymeric Al complexes of the respective molecular weight range. By comparing the surface area of one peak to the total surface area of all peaks obtained thus allows a direct determination of the content of polymeric Al complexes of the corresponding molecular weight range in the total amount of the formed polymeric Al complexes in the aluminum salt of formula (I), and in particular of formula (Ia).

Peak 4 contains the polymeric Al complexes having a low molecular weight that are significant for the antiperspirant action. With respect to the antiperspirant action, it is therefore advantageous according to the invention if the surface area proportion of the peak surface area 4 is within a certain range in the chromatogram compared to the total surface area of all peak surface areas 1 to 5, or 1 to 6. Preferred antiperspirant cosmetic agents according to the invention are therefore characterized by comprising at least one aluminum salt of formula (I), and in particular of formula (Ia), having a peak surface area proportion of peak 4 to the total surface area of all peaks in the chromatogram of 30 to 80%, especially of 32 to 70%, preferably of 35 to 60%, and in particular of 40 to 55%. The peak surface area proportion of peak 4 in relation to the total surface area of all peaks in the chromatogram was determined by way of size exclusion chromatography using an Agilent Zorbax PSM 60S column, using 0.02 M HCl as the eluent. The total surface area of all peaks here refers to the sum of all peaks obtained for the aluminum salt in the chromatogram. The use of such aluminum salts has been found to be particularly advantageous with respect to the reduced residue build-up and the improved dryness sensation.

The at least one aluminum salt of formula (I), and in particular of formula (Ia), is preferably used in certain quantity ranges. It is therefore advantageous according to the invention if the cosmetic agent, based on the total weight thereof, comprises 2.0 to 6.0 wt. %, especially 2.5 to 5.5 wt. %, preferably 3.0 to 5.5 wt. %, and in particular 3.5 to 5.0 wt. % of at least one aluminum salt of formula (I), and in particular of formula (Ia). Using the aforementioned total amounts of the aluminum salt of formula (I), and in particular of formula (Ia), results in outstanding antiperspirant power, without creating incompatibilities with other ingredients of the cosmetic agents according to the invention or excessive residue build-up on textiles.

As a second essential component b), the antiperspirant cosmetic agent according to the invention comprises at least one non-volatile ester.

Within the scope of the present invention, it is preferred if the at least one non-volatile ester has a certain refractive index $R_f$. Preferred antiperspirant cosmetic agents according to the invention are thus characterized by comprising at least one non-volatile ester having a refractive index $R_f$, measured at 20° C., of 1.481 to 1.590, especially of 1.481 to 1.560, preferably of 1.481 to 1.540, and in particular of 1.481 to 1.500. The use of at least one non-volatile ester having a refractive index $R_f$ in the aforementioned range has proven to be particularly advantageous with respect to the reduced residue build-up. The refractive index $R_f$ can be determined using a refractometer, for example.

Within the scope of the present invention, it is preferred if the agent comprises at least two non-volatile esters having differing refractive indices $R_f$ in certain weight ratios. It is thus preferred within the scope of the present invention if the cosmetic agent comprises at least one first non-volatile ester (E1) having a refractive index $R_f$, measured at 20° C., of 1.481 to 1.485, and at least one second non-volatile ester (E2) having a refractive index $R_f$, measured at 20° C., of 1.486 to 1.500, and in particular $C_{12}$ to $C_{15}$ alkyl benzoate (E1) and phenoxyethyl caprylate (E2), in a weight ratio of E1 :E2 of 1:10 to 10:1, especially of 1:8 to 8:1, preferably of 1:6 to 1:1, and of 1:5 to 1:3. The $C_{12}$ to $C_{15}$ alkyl benzoate has a refractive index $R_f$ at 20° C. of 1.483 to 1.485, and the phenoxyethyl caprylate has a refractive index $R_f$ at 20° C. of 1.486 to 1.491. Use of the aforementioned weight ratios has been found to be particularly advantageous with respect to the reduced residue build-up and the improved dryness sensation.

It has furthermore been found to be advantageous within the scope of the present invention to use certain non-volatile esters. It is thus particularly preferred within the scope of the present invention if the cosmetic agent comprises at least one non-volatile ester from the group consisting of $C_{12}$ to $C_{15}$ alkyl benzoate, phenoxyethyl caprylate, ethylhexyl palmitate, isopropyl myristate and the mixtures thereof, and in particular $C_{12}$ to $C_{15}$ alkyl benzoate and phenoxyethyl caprylate and ethylhexyl palmitate and isopropyl myristate. Use of the aforementioned compounds, in combination with the at least one aluminum salt of formula (I), and in particular of formula (Ia), and the volatile silicone compound, results in an outstanding antiperspirant action and in reduced residue build-up. Using a mixture of all aforementioned non-volatile esters can further improve the dryness sensation, without adversely affecting the antiperspirant action or residue build-up.

Within the scope of the present invention, it is furthermore preferred if the at least one non-volatile ester b) is used in certain quantity ranges. Preferred antiperspirant cosmetic agents according to the invention are thus characterized by comprising, based on the total weight thereof, 5.0 to 22 wt. %, especially 5.0 to 20 wt. %, preferably 5.0 to 15 wt. %, and in particular 5.0 to 10 wt. % of at least one non-volatile ester, in particular $C_{12}$ to $C_{15}$ alkyl benzoate and/or phenoxyethyl caprylate and/or ethylhexyl palmitate and/or isopropyl myristate. Use of the aforementioned amounts of the at least one non-volatile ester, and in particular of $C_{12}$ to $C_{15}$ alkyl benzoate and/or phenoxyethyl caprylate and/or ethylhexyl palmitate and/or isopropyl myristate, has been found to be particularly advantageous with respect to the reduced residue build-up and the improved dryness sensation.

It has been found to be advantageous according to the invention if the antiperspirant cosmetic agents according to the invention have a certain weight ratio of aluminum salt of formula (I), and in particular of formula (Ia), to the at least one non-volatile ester, and in particular $C_{12}$ to $C_{15}$ alkyl benzoate and/or phenoxyethyl caprylate and/or ethylhexyl palmitate and/or isopropyl myristate. It is thus preferred within the scope of the present invention if the cosmetic agents have a certain weight ratio of the at least one aluminum salt of formula (I), and in particular of formula (Ia), to the at least one non-volatile ester, and in particular $C_{12}$ to $C_{15}$ alkyl benzoate and/or phenoxyethyl caprylate and/or ethylhexyl palmitate and/or isopropyl myristate, of 2:1 to 1:5, especially of 1:1 to 1:4, preferably of 1:1.2 to 1:3, and in particular of 1:1.2 to 1:2. Use of the aforementioned weight ratios results in an improved antiperspirant action, reduced residue build-up, and an improved dryness sensation.

As a third essential component c), the antiperspirant cosmetic agent according to the invention comprises at least one volatile silicone compound.

It is preferred if certain volatile silicone compounds are used. Preferred cosmetic agents according to the invention are thus characterized by comprising at least one volatile silicone compound, selected from the group consisting of cyclic silicone compounds having 2 to 10, and in particular 3 to 6, siloxane units, linear silicone compounds having 2 to 10, and in particular 6 to 10, siloxane units, and the mixtures thereof.

In this connection it is advantageous if the at least one volatile silicone compound is selected from cyclic silicone compounds having 3 to 6 siloxane units, and in particular cyclopentasiloxane. Use of cyclic silicone compounds, and in particular cyclopentasiloxane, in combination with at least one non-volatile ester and the above-listed aluminum salts, has proven to be particularly advantageous with respect to the reduced residue build-up and the improved dryness sensation.

Within the scope of the present invention, it has proven to be advantageous to use the at least one volatile silicone compound in certain quantity ranges. Preferred cosmetic agents according to the present invention are thus characterized by comprising, based on the total weight thereof, 1.0 to 10 wt. %, especially 1.5 to 8.0 wt. %, preferably 2.0 to 6.0 wt. %, and in particular 2.0 to 5.0 wt. % of at least one volatile silicone compound, and in particular cyclopentasiloxane. Use of the aforementioned amounts of the at least one volatile silicone compound, and in particular cyclopentasiloxane, has been found to be particularly advantageous with respect to the reduced residue build-up and the improved dryness sensation.

It has been found to be advantageous according to the invention if the antiperspirant cosmetic agents according to the invention have a certain weight ratio of aluminum salt of formula (I), and in particular of formula (Ia), to the at least one volatile silicone compound, and in particular cyclopentasiloxane. It is thus preferred within the scope of the present invention if the cosmetic agents have a weight ratio of the at least one aluminum salt of formula (I), and in particular of formula (Ia), to the at least one volatile silicone compound, and in particular cyclopentasiloxane, of 5:1 to 1:3, especially of 4:1 to 1:2, preferably of 3:1 to 1:1.5, and in particular of 2.5:1 to 1:1.1. Use of the aforementioned weight ratios results in an improved antiperspirant action, reduced residue build-up, and an improved dryness sensation.

As a fourth essential component d), the antiperspirant cosmetic agent according to the invention comprises at least one propellant.

The antiperspirant cosmetic agents according to the invention are formulated as aerosols and thus comprise at least one propellant. It is preferred to use certain propellants within the scope of the present invention. Advantageous antiperspirant cosmetic agents according to the invention are thus characterized by comprising at least one propellant selected from the group consisting of propane, propene, n-butane, iso-butane, iso-butene, n-pentane, pentene, iso-pentane, iso-pentene, methane, ethane, dimethyl ether, nitrogen, air, oxygen, nitrous oxide, 1,1,1,3-tetrafluoroethane, heptafluoro-n-propane, perfluoroethane, monochlorodifluoromethane, 1,1-difluoroethane, tetrafluoropropene, and the mixtures thereof, and in particular propane and/or n-butane and/or iso-butane. It is furthermore also possible according to the invention to use mixtures of the aforementioned propellants with hydrophilic propellants, such as carbon dioxide and/or dimethyl ether.

So as to ensure sufficient sprayability and complete removal of the agents according to the invention, the propellant is preferably used in certain quantity ranges. It is therefore advantageous within the scope of the present invention if the cosmetic agent, based on the total weight thereof, comprises 20 to 80 wt. %, especially 55 to 80 wt. %, preferably 60 to 80 wt. %, and in particular 65 to 80 wt. % of at least one propellant, and in particular propane and/or n-butane and/or iso-butane.

Pressure-resistant containers that may be used for such aerosols include vessels made of metal (aluminum, tinplate, tin), protected or shatterproof plastic, or glass, which are coated with plastic on the outside, in the selection of which pressure resistance, fracture strength, corrosion resistance, ease of filling, as well as aesthetic aspects, handling, printability and the like play a role. Special inside protection coatings ensure corrosion resistance against the cosmetic agent according to the invention present in the pressurized container. It is particularly preferred if the valves used comprise a valve plate that is coated on the inside, wherein the paint and valve material are compatible with each other. If aluminum valves are used, the valve plates thereof may be coated on the inside, for example with a Micoflex coating. If tinplate valves are used according to the invention, the valve plates thereof may be coated on the inside with polyethylene terephthalate (PET), for example. The sizes of the aerosol droplets and the respective size distribution can be set for a particular spraying device by way of the quantity ratio of propellant to the remaining components of the cosmetic agents.

The cosmetic agent according to the invention furthermore has a certain weight ratio of the at least one non-volatile ester to the at least one volatile silicone compound. It is preferred according to the invention, however, if weight ratios in narrow ranges are used. It is therefore advantageous according to the invention if the weight ratio of the at least one non-volatile ester b) to the at least one volatile silicone compound d) in the agent is 5:1 to 1:1, especially 4:1 to 1:1, preferably 3:1 to 1:1, and in particular 2:1 to 1.2:1. Use of the aforementioned weight ratios of the at least one non-volatile ester to the at least one volatile silicone compound results in reduced residue build-up and an improved dryness sensation. In addition, the antiperspirant action of the aforementioned aluminum salt is not adversely affected.

It may be preferred within the scope of the present invention if the antiperspirant cosmetic agent comprises additional ingredients, selected from the group of triethyl citrate, propylene carbonate and bentonite, and the mixtures thereof.

It has proven to be advantageous within the scope of the present invention to furthermore add triethyl citrate and/or propylene carbonate to the antiperspirant cosmetic agents according to the invention. Preferred antiperspirant cosmetic agents according to the present invention are thus characterized by additionally comprising, based on the total weight thereof, 0.05 to 5.0 wt. %, especially 0.1 to 3.0 wt. %, preferably 0.15 to 2.0 wt. %, and in particular 0.2 to 1.5 wt. % triethyl citrate and/or propylene carbonate.

The antiperspirant cosmetic agents according to the invention are preferably formulated as flowable preparations. The agents should be formulated such they are not only easy to spray as an aerosol, but also sufficiently viscous, so that they remain at the site of action, and in particular under the armpit, during the residence time and do not run or are not excessively transferred to clothing. Preferred agents according to the invention thus additionally comprise at least one thickening agent, and in particular bentonite. Advantageous antiperspirant cosmetic agents are thus characterized by additionally comprising, based on the total weight thereof, 0.1 to 2.0 wt. %, especially 0.2 to 1.5 wt. %, preferably 0.3 to 1.0 wt. %, and in particular 0.4 to 0.8 wt. % bentonite.

It has been found to be advantageous within the scope of the present invention if the antiperspirant cosmetic agents according to the invention are formulated to be anhydrous. The term "anhydrous" within the scope of the present invention shall be understood to mean agents that comprise less than 1 wt. %, especially less than 0.5 wt. %, and in particular 0 wt. % water, based on the total weight of the agents. The calculation of the water content, however, does not take constitutional water, hydration water or similarly molecularly bound water of the components used, and in particular of the aluminum salts of formulas (I) and (Ia), into account. Preferred antiperspirant cosmetic agents according to the invention are thus characterized by being anhydrous.

Furthermore, it has proven to be advantageous within the scope of the present invention if the antiperspirant cosmetic agents according to the invention do not comprise any alkoxylated, in particular ethoxylated and/or propoxylated, silicone compounds. These are understood to mean silicone compounds comprising at least one ethoxy group and/or propoxy group in the backbone and/or on the side chains. Preferred embodiments of the agents according to the invention are thus characterized by comprising no alkoxylated, and in particular no ethoxylated and/or propoxylated silicones.

The following tables list particularly preferred embodiments AF 1 to AF 192 of the antiperspirant cosmetic agents according to the invention (all information is in wt. %, unless indicated otherwise). Embodiments AF 1 to AF 192 are anhydrous, do not comprise any alkoxylated, in particular ethoxylated and/or propoxylated, silicones, and have a weight ratio of the non-volatile ester to the volatile silicone compound of 2:1 to 1.2:1.

|  | AF 1 | AF 2 | AF 3 | AF 4 |
|---|---|---|---|---|
| Aluminum salt of formula (I) | 2.0 to 6.0 | 2.5 to 5.5 | 3.0 to 5.5 | 3.5 to 5.0 |
| Non-volatile ester | 5.0 to 22 | 5.0 to 20 | 5.0 to 15 | 5.0 to 10 |
| Volatile silicone compound | 1.0 to 10 | 1.5 to 8.0 | 2.0 to 6.0 | 2.0 to 5.0 |
| Propellant | to make 100 | to make 100 | to make 100 | to make 100 |

|  | AF 5 | AF 6 | AF 7 | AF 8 |
|---|---|---|---|---|
| Aluminum salt of formula (I) [1] | 2.0 to 6.0 | 2.5 to 5.5 | 3.0 to 5.5 | 3.5 to 5.0 |
| Non-volatile ester | 5.0 to 22 | 5.0 to 20 | 5.0 to 15 | 5.0 to 10 |
| Volatile silicone compound | 1.0 to 10 | 1.5 to 8.0 | 2.0 to 6.0 | 2.0 to 5.0 |
| Propellant | to make 100 | to make 100 | to make 100 | to make 100 |

|  | AF 9 | AF 10 | AF 11 | AF 12 |
|---|---|---|---|---|
| Aluminum salt of formula (I) [2] | 2.0 to 6.0 | 2.5 to 5.5 | 3.0 to 5.5 | 3.5 to 5.0 |
| Non-volatile ester | 5.0 to 22 | 5.0 to 20 | 5.0 to 15 | 5.0 to 10 |
| Volatile silicone compound | 1.0 to 10 | 1.5 to 8.0 | 2.0 to 6.0 | 2.0 to 5.0 |
| Propellant | to make 100 | to make 100 | to make 100 | to make 100 |

|  | AF 13 | AF 14 | AF 15 | AF 16 |
|---|---|---|---|---|
| Aluminum salt of formula (Ia) | 2.0 to 6.0 | 2.5 to 5.5 | 3.0 to 5.5 | 3.5 to 5.0 |
| Non-volatile ester | 5.0 to 22 | 5.0 to 20 | 5.0 to 15 | 5.0 to 10 |
| Volatile silicone compound | 1.0 to 10 | 1.5 to 8.0 | 2.0 to 6.0 | 2.0 to 5.0 |
| Propellant | to make 100 | to make 100 | to make 100 | to make 100 |

|  | AF 17 | AF 18 | AF 19 | AF 20 |
|---|---|---|---|---|
| Aluminum salt of formula (Ia) [1] | 2.0 to 6.0 | 2.5 to 5.5 | 3.0 to 5.5 | 3.5 to 5.0 |
| Non-volatile ester | 5.0 to 22 | 5.0 to 20 | 5.0 to 15 | 5.0 to 10 |
| Volatile silicone compound | 1.0 to 10 | 1.5 to 8.0 | 2.0 to 6.0 | 2.0 to 5.0 |
| Propellant | to make 100 | to make 100 | to make 100 | to make 100 |

|  | AF 21 | AF 22 | AF 23 | AF 24 |
|---|---|---|---|---|
| Aluminum salt of formula (Ia) [2] | 2.0 to 6.0 | 2.5 to 5.5 | 3.0 to 5.5 | 3.5 to 5.0 |
| Non-volatile ester | 5.0 to 22 | 5.0 to 20 | 5.0 to 15 | 5.0 to 10 |
| Volatile silicone compound | 1.0 to 10 | 1.5 to 8.0 | 2.0 to 6.0 | 2.0 to 5.0 |
| Propellant | to make 100 | to make 100 | to make 100 | to make 100 |

|  | AF 25 | AF 26 | AF 27 | AF 28 |
|---|---|---|---|---|
| Aluminum salt of formula (I) | 2.0 to 6.0 | 2.5 to 5.5 | 3.0 to 5.5 | 3.5 to 5.0 |
| Non-volatile ester [3] | 5.0 to 22 | 5.0 to 20 | 5.0 to 15 | 5.0 to 10 |
| Volatile silicone compound | 1.0 to 10 | 1.5 to 8.0 | 2.0 to 6.0 | 2.0 to 5.0 |
| Propellant | to make 100 | to make 100 | to make 100 | to make 100 |

|  | AF 29 | AF 30 | AF 31 | AF 32 |
|---|---|---|---|---|
| Aluminum salt of formula (I) [1] | 2.0 to 6.0 | 2.5 to 5.5 | 3.0 to 5.5 | 3.5 to 5.0 |
| Non-volatile ester [3] | 5.0 to 22 | 5.0 to 20 | 5.0 to 15 | 5.0 to 10 |
| Volatile silicone compound | 1.0 to 10 | 1.5 to 8.0 | 2.0 to 6.0 | 2.0 to 5.0 |
| Propellant | to make 100 | to make 100 | to make 100 | to make 100 |

|  | AF 33 | AF 34 | AF 35 | AF 36 |
|---|---|---|---|---|
| Aluminum salt of formula (I) [2] | 2.0 to 6.0 | 2.5 to 5.5 | 3.0 to 5.5 | 3.5 to 5.0 |
| Non-volatile ester [3] | 5.0 to 22 | 5.0 to 20 | 5.0 to 15 | 5.0 to 10 |
| Volatile silicone compound | 1.0 to 10 | 1.5 to 8.0 | 2.0 to 6.0 | 2.0 to 5.0 |
| Propellant | to make 100 | to make 100 | to make 100 | to make 100 |

|  | AF 37 | AF 38 | AF 39 | AF 40 |
|---|---|---|---|---|
| Aluminum salt of formula (Ia) | 2.0 to 6.0 | 2.5 to 5.5 | 3.0 to 5.5 | 3.5 to 5.0 |
| Non-volatile ester [3] | 5.0 to 22 | 5.0 to 20 | 5.0 to 15 | 5.0 to 10 |

-continued

|  |  |  |  |  |
|---|---|---|---|---|
| Volatile silicone compound | 1.0 to 10 | 1.5 to 8.0 | 2.0 to 6.0 | 2.0 to 5.0 |
| Propellant | to make 100 | to make 100 | to make 100 | to make 100 |
|  | AF 41 | AF 42 | AF 43 | AF 44 |
| Aluminum salt of formula (Ia) [1] | 2.0 to 6.0 | 2.5 to 5.5 | 3.0 to 5.5 | 3.5 to 5.0 |
| Non-volatile ester [3] | 5.0 to 22 | 5.0 to 20 | 5.0 to 15 | 5.0 to 10 |
| Volatile silicone compound | 1.0 to 10 | 1.5 to 8.0 | 2.0 to 6.0 | 2.0 to 5.0 |
| Propellant | to make 100 | to make 100 | to make 100 | to make 100 |
|  | AF 45 | AF 46 | AF 47 | AF 48 |
| Aluminum salt of formula (Ia) | 2.0 to 6.0 | 2.5 to 5.5 | 3.0 to 5.5 | 3.5 to 5.0 |
| Non-volatile ester [3] | 5.0 to 22 | 5.0 to 20 | 5.0 to 15 | 5.0 to 10 |
| Volatile silicone compound | 1.0 to 10 | 1.5 to 8.0 | 2.0 to 6.0 | 2.0 to 5.0 |
| Propellant | to make 100 | to make 100 | to make 100 | to make 100 |
|  | AF 49 | AF 50 | AF 51 | AF 52 |
| Aluminum salt of formula (I) | 2.0 to 6.0 | 2.5 to 5.5 | 3.0 to 5.5 | 3.5 to 5.0 |
| Non-volatile ester [4] | 5.0 to 22 | 5.0 to 20 | 5.0 to 15 | 5.0 to 10 |
| Volatile silicone compound | 1.0 to 10 | 1.5 to 8.0 | 2.0 to 6.0 | 2.0 to 5.0 |
| Propellant | to make 100 | to make 100 | to make 100 | to make 100 |
|  | AF 53 | AF 54 | AF 55 | AF 56 |
| Aluminum salt of formula (I) [1] | 2.0 to 6.0 | 2.5 to 5.5 | 3.0 to 5.5 | 3.5 to 5.0 |
| Non-volatile ester [4] | 5.0 to 22 | 5.0 to 20 | 5.0 to 15 | 5.0 to 10 |
| Volatile silicone compound | 1.0 to 10 | 1.5 to 8.0 | 2.0 to 6.0 | 2.0 to 5.0 |
| Propellant | to make 100 | to make 100 | to make 100 | to make 100 |
|  | AF 57 | AF 58 | AF 59 | AF 60 |
| Aluminum salt of formula (I) [2] | 2.0 to 6.0 | 2.5 to 5.5 | 3.0 to 5.5 | 3.5 to 5.0 |
| Non-volatile ester [4] | 5.0 to 22 | 5.0 to 20 | 5.0 to 15 | 5.0 to 10 |
| Volatile silicone compound | 1.0 to 10 | 1.5 to 8.0 | 2.0 to 6.0 | 2.0 to 5.0 |
| Propellant | to make 100 | to make 100 | to make 100 | to make 100 |
|  | AF 61 | AF 62 | AF 63 | AF 64 |
| Aluminum salt of formula (Ia) | 2.0 to 6.0 | 2.5 to 5.5 | 3.0 to 5.5 | 3.5 to 5.0 |
| Non-volatile ester [4] | 5.0 to 22 | 5.0 to 20 | 5.0 to 15 | 5.0 to 10 |
| Volatile silicone compound | 1.0 to 10 | 1.5 to 8.0 | 2.0 to 6.0 | 2.0 to 5.0 |
| Propellant | to make 100 | to make 100 | to make 100 | to make 100 |
|  | AF 65 | AF 66 | AF 67 | AF 68 |
| Aluminum salt of formula (Ia) [1] | 2.0 to 6.0 | 2.5 to 5.5 | 3.0 to 5.5 | 3.5 to 5.0 |
| Non-volatile ester [4] | 5.0 to 22 | 5.0 to 20 | 5.0 to 15 | 5.0 to 10 |
| Volatile silicone compound | 1.0 to 10 | 1.5 to 8.0 | 2.0 to 6.0 | 2.0 to 5.0 |
| Propellant | to make 100 | to make 100 | to make 100 | to make 100 |
|  | AF 69 | AF 70 | AF 71 | AF 72 |
| Aluminum salt of formula (Ia) [2] | 2.0 to 6.0 | 2.5 to 5.5 | 3.0 to 5.5 | 3.5 to 5.0 |
| Non-volatile ester [4] | 5.0 to 22 | 5.0 to 20 | 5.0 to 15 | 5.0 to 10 |
| Volatile silicone compound | 1.0 to 10 | 1.5 to 8.0 | 2.0 to 6.0 | 2.0 to 5.0 |
| Propellant | to make 100 | to make 100 | to make 100 | to make 100 |
|  | AF 49 | AF 50 | AF 51 | AF 52 |
| Aluminum salt of formula (I) | 2.0 to 6.0 | 2.5 to 5.5 | 3.0 to 5.5 | 3.5 to 5.0 |
| Non-volatile ester [5] | 5.0 to 22 | 5.0 to 20 | 5.0 to 15 | 5.0 to 10 |
| Volatile silicone compound | 1.0 to 10 | 1.5 to 8.0 | 2.0 to 6.0 | 2.0 to 5.0 |
| Propellant | to make 100 | to make 100 | to make 100 | to make 100 |
|  | AF 53 | AF 54 | AF 55 | AF 56 |
| Aluminum salt of formula (I) [1] | 2.0 to 6.0 | 2.5 to 5.5 | 3.0 to 5.5 | 3.5 to 5.0 |
| Non-volatile ester [5] | 5.0 to 22 | 5.0 to 20 | 5.0 to 15 | 5.0 to 10 |
| Volatile silicone compound | 1.0 to 10 | 1.5 to 8.0 | 2.0 to 6.0 | 2.0 to 5.0 |
| Propellant | to make 100 | to make 100 | to make 100 | to make 100 |
|  | AF 57 | AF 58 | AF 59 | AF 60 |
| Aluminum salt of formula (I) [2] | 2.0 to 6.0 | 2.5 to 5.5 | 3.0 to 5.5 | 3.5 to 5.0 |
| Non-volatile ester [5] | 5.0 to 22 | 5.0 to 20 | 5.0 to 15 | 5.0 to 10 |

-continued

|  | | | | |
|---|---|---|---|---|
| Volatile silicone compound | 1.0 to 10 | 1.5 to 8.0 | 2.0 to 6.0 | 2.0 to 5.0 |
| Propellant | to make 100 | to make 100 | to make 100 | to make 100 |

|  | AF 61 | AF 62 | AF 63 | AF 64 |
|---|---|---|---|---|
| Aluminum salt of formula (Ia) | 2.0 to 6.0 | 2.5 to 5.5 | 3.0 to 5.5 | 3.5 to 5.0 |
| Non-volatile ester [5] | 5.0 to 22 | 5.0 to 20 | 5.0 to 15 | 5.0 to 10 |
| Volatile silicone compound | 1.0 to 10 | 1.5 to 8.0 | 2.0 to 6.0 | 2.0 to 5.0 |
| Propellant | to make 100 | to make 100 | to make 100 | to make 100 |

|  | AF 65 | AF 66 | AF 67 | AF 68 |
|---|---|---|---|---|
| Aluminum salt of formula (Ia) | 2.0 to 6.0 | 2.5 to 5.5 | 3.0 to 5.5 | 3.5 to 5.0 |
| Non-volatile ester [5] | 5.0 to 22 | 5.0 to 20 | 5.0 to 15 | 5.0 to 10 |
| Volatile silicone compound | 1.0 to 10 | 1.5 to 8.0 | 2.0 to 6.0 | 2.0 to 5.0 |
| Propellant | to make 100 | to make 100 | to make 100 | to make 100 |

|  | AF 69 | AF 70 | AF 71 | AF 72 |
|---|---|---|---|---|
| Aluminum salt of formula (Ia) | 2.0 to 6.0 | 2.5 to 5.5 | 3.0 to 5.5 | 3.5 to 5.0 |
| Non-volatile ester [5] | 5.0 to 22 | 5.0 to 20 | 5.0 to 15 | 5.0 to 10 |
| Volatile silicone compound | 1.0 to 10 | 1.5 to 8.0 | 2.0 to 6.0 | 2.0 to 5.0 |
| Propellant | to make 100 | to make 100 | to make 100 | to make 100 |

|  | AF 73 | AF 74 | AF 75 | AF 76 |
|---|---|---|---|---|
| Aluminum salt of formula (I) | 2.0 to 6.0 | 2.5 to 5.5 | 3.0 to 5.5 | 3.5 to 5.0 |
| Non-volatile ester | 5.0 to 22 | 5.0 to 20 | 5.0 to 15 | 5.0 to 10 |
| Volatile silicone compound [6] | 1.0 to 10 | 1.5 to 8.0 | 2.0 to 6.0 | 2.0 to 5.0 |
| Propellant | to make 100 | to make 100 | to make 100 | to make 100 |

|  | AF 77 | AF 78 | AF 79 | AF 80 |
|---|---|---|---|---|
| Aluminum salt of formula (I) [1] | 2.0 to 6.0 | 2.5 to 5.5 | 3.0 to 5.5 | 3.5 to 5.0 |
| Non-volatile ester | 5.0 to 22 | 5.0 to 20 | 5.0 to 15 | 5.0 to 10 |
| Volatile silicone compound [6] | 1.0 to 10 | 1.5 to 8.0 | 2.0 to 6.0 | 2.0 to 5.0 |
| Propellant | to make 100 | to make 100 | to make 100 | to make 100 |

|  | AF 81 | AF 82 | AF 83 | AF 84 |
|---|---|---|---|---|
| Aluminum salt of formula (I) [2] | 2.0 to 6.0 | 2.5 to 5.5 | 3.0 to 5.5 | 3.5 to 5.0 |
| Non-volatile ester | 5.0 to 22 | 5.0 to 20 | 5.0 to 15 | 5.0 to 10 |
| Volatile silicone compound [6] | 1.0 to 10 | 1.5 to 8.0 | 2.0 to 6.0 | 2.0 to 5.0 |
| Propellant | to make 100 | to make 100 | to make 100 | to make 100 |

|  | AF 85 | AF 86 | AF 87 | AF 88 |
|---|---|---|---|---|
| Aluminum salt of formula (Ia) | 2.0 to 6.0 | 2.5 to 5.5 | 3.0 to 5.5 | 3.5 to 5.0 |
| Non-volatile ester | 5.0 to 22 | 5.0 to 20 | 5.0 to 15 | 5.0 to 10 |
| Volatile silicone compound [6] | 1.0 to 10 | 1.5 to 8.0 | 2.0 to 6.0 | 2.0 to 5.0 |
| Propellant | to make 100 | to make 100 | to make 100 | to make 100 |

|  | AF 89 | AF 90 | AF 91 | AF 92 |
|---|---|---|---|---|
| Aluminum salt of formula (Ia) | 2.0 to 6.0 | 2.5 to 5.5 | 3.0 to 5.5 | 3.5 to 5.0 |
| Non-volatile ester | 5.0 to 22 | 5.0 to 20 | 5.0 to 15 | 5.0 to 10 |
| Volatile silicone compound [6] | 1.0 to 10 | 1.5 to 8.0 | 2.0 to 6.0 | 2.0 to 5.0 |
| Propellant | to make 100 | to make 100 | to make 100 | to make 100 |

|  | AF 93 | AF 94 | AF 95 | AF 96 |
|---|---|---|---|---|
| Aluminum salt of formula (Ia) [2] | 2.0 to 6.0 | 2.5 to 5.5 | 3.0 to 5.5 | 3.5 to 5.0 |
| Non-volatile ester | 5.0 to 22 | 5.0 to 20 | 5.0 to 15 | 5.0 to 10 |
| Volatile silicone compound [6] | 1.0 to 10 | 1.5 to 8.0 | 2.0 to 6.0 | 2.0 to 5.0 |
| Propellant | to make 100 | to make 100 | to make 100 | to make 100 |

|  | AF 97 | AF 98 | AF 99 | AF 100 |
|---|---|---|---|---|
| Aluminum salt of formula (I) | 2.0 to 6.0 | 2.5 to 5.5 | 3.0 to 5.5 | 3.5 to 5.0 |
| Non-volatile ester | 5.0 to 22 | 5.0 to 20 | 5.0 to 15 | 5.0 to 10 |
| Volatile silicone compound [7] | 1.0 to 10 | 1.5 to 8.0 | 2.0 to 6.0 | 2.0 to 5.0 |
| Propellant | to make 100 | to make 100 | to make 100 | to make 100 |

|  | AF 101 | AF 102 | AF 103 | AF 104 |
|---|---|---|---|---|
| Aluminum salt of formula (I) [1] | 2.0 to 6.0 | 2.5 to 5.5 | 3.0 to 5.5 | 3.5 to 5.0 |
| Non-volatile ester | 5.0 to 22 | 5.0 to 20 | 5.0 to 15 | 5.0 to 10 |

|  | | | | |
|---|---|---|---|---|
| Volatile silicone compound [7] | 1.0 to 10 | 1.5 to 8.0 | 2.0 to 6.0 | 2.0 to 5.0 |
| Propellant | to make 100 | to make 100 | to make 100 | to make 100 |
|  | AF 105 | AF 106 | AF 107 | AF 108 |
| Aluminum salt of formula (I) [2] | 2.0 to 6.0 | 2.5 to 5.5 | 3.0 to 5.5 | 3.5 to 5.0 |
| Non-volatile ester | 5.0 to 22 | 5.0 to 20 | 5.0 to 15 | 5.0 to 10 |
| Volatile silicone compound [7] | 1.0 to 10 | 1.5 to 8.0 | 2.0 to 6.0 | 2.0 to 5.0 |
| Propellant | to make 100 | to make 100 | to make 100 | to make 100 |
|  | AF 109 | AF 110 | AF 111 | AF 112 |
| Aluminum salt of formula (Ia) | 2.0 to 6.0 | 2.5 to 5.5 | 3.0 to 5.5 | 3.5 to 5.0 |
| Non-volatile ester | 5.0 to 22 | 5.0 to 20 | 5.0 to 15 | 5.0 to 10 |
| Volatile silicone compound [7] | 1.0 to 10 | 1.5 to 8.0 | 2.0 to 6.0 | 2.0 to 5.0 |
| Propellant | to make 100 | to make 100 | to make 100 | to make 100 |
|  | AF 113 | AF 114 | AF 115 | AF 116 |
| Aluminum salt of formula (Ia) [1] | 2.0 to 6.0 | 2.5 to 5.5 | 3.0 to 5.5 | 3.5 to 5.0 |
| Non-volatile ester | 5.0 to 22 | 5.0 to 20 | 5.0 to 15 | 5.0 to 10 |
| Volatile silicone compound [7] | 1.0 to 10 | 1.5 to 8.0 | 2.0 to 6.0 | 2.0 to 5.0 |
| Propellant | to make 100 | to make 100 | to make 100 | to make 100 |
|  | AF 117 | AF 118 | AF 119 | AF 120 |
| Aluminum salt of formula (Ia) [2] | 2.0 to 6.0 | 2.5 to 5.5 | 3.0 to 5.5 | 3.5 to 5.0 |
| Non-volatile ester | 5.0 to 22 | 5.0 to 20 | 5.0 to 15 | 5.0 to 10 |
| Volatile silicone compound [7] | 1.0 to 10 | 1.5 to 8.0 | 2.0 to 6.0 | 2.0 to 5.0 |
| Propellant | to make 100 | to make 100 | to make 100 | to make 100 |
|  | AF 121 | AF 122 | AF 123 | AF 124 |
| Aluminum salt of formula (I) | 2.0 to 6.0 | 2.5 to 5.5 | 3.0 to 5.5 | 3.5 to 5.0 |
| Non-volatile ester [5] | 5.0 to 22 | 5.0 to 20 | 5.0 to 15 | 5.0 to 10 |
| Volatile silicone compound [7] | 1.0 to 10 | 1.5 to 8.0 | 2.0 to 6.0 | 2.0 to 5.0 |
| Propellant [8] | to make 100 | to make 100 | to make 100 | to make 100 |
|  | AF 125 | AF 126 | AF 127 | AF 128 |
| Aluminum salt of formula (I) [1] | 2.0 to 6.0 | 2.5 to 5.5 | 3.0 to 5.5 | 3.5 to 5.0 |
| Non-volatile ester [5] | 5.0 to 22 | 5.0 to 20 | 5.0 to 15 | 5.0 to 10 |
| Volatile silicone compound [7] | 1.0 to 10 | 1.5 to 8.0 | 2.0 to 6.0 | 2.0 to 5.0 |
| Propellant [8] | to make 100 | to make 100 | to make 100 | to make 100 |
|  | AF 129 | AF 130 | AF 131 | AF 132 |
| Aluminum salt of formula (I) [2] | 2.0 to 6.0 | 2.5 to 5.5 | 3.0 to 5.5 | 3.5 to 5.0 |
| Non-volatile ester [5] | 5.0 to 22 | 5.0 to 20 | 5.0 to 15 | 5.0 to 10 |
| Volatile silicone compound [7] | 1.0 to 10 | 1.5 to 8.0 | 2.0 to 6.0 | 2.0 to 5.0 |
| Propellant [8] | to make 100 | to make 100 | to make 100 | to make 100 |
|  | AF 133 | AF 134 | AF 135 | AF 136 |
| Aluminum salt of formula (Ia) | 2.0 to 6.0 | 2.5 to 5.5 | 3.0 to 5.5 | 3.5 to 5.0 |
| Non-volatile ester [5] | 5.0 to 22 | 5.0 to 20 | 5.0 to 15 | 5.0 to 10 |
| Volatile silicone compound [7] | 1.0 to 10 | 1.5 to 8.0 | 2.0 to 6.0 | 2.0 to 5.0 |
| Propellant [8] | to make 100 | to make 100 | to make 100 | to make 100 |
|  | AF 137 | AF 138 | AF 139 | AF 140 |
| Aluminum salt of formula (Ia) [1] | 2.0 to 6.0 | 2.5 to 5.5 | 3.0 to 5.5 | 3.5 to 5.0 |
| Non-volatile ester [5] | 5.0 to 22 | 5.0 to 20 | 5.0 to 15 | 5.0 to 10 |
| Volatile silicone compound [7] | 1.0 to 10 | 1.5 to 8.0 | 2.0 to 6.0 | 2.0 to 5.0 |
| Propellant [8] | to make 100 | to make 100 | to make 100 | to make 100 |
|  | AF 141 | AF 142 | AF 143 | AF 144 |
| Aluminum salt of formula (Ia) [2] | 2.0 to 6.0 | 2.5 to 5.5 | 3.0 to 5.5 | 3.5 to 5.0 |
| Non-volatile ester [5] | 5.0 to 22 | 5.0 to 20 | 5.0 to 15 | 5.0 to 10 |
| Volatile silicone compound [7] | 1.0 to 10 | 1.5 to 8.0 | 2.0 to 6.0 | 2.0 to 5.0 |
| Propellant [8] | to make 100 | to make 100 | to make 100 | to make 100 |
|  | AF 145 | AF 146 | AF 147 | AF 148 |
| Aluminum salt of formula (I) | 2.0 to 6.0 | 2.5 to 5.5 | 3.0 to 5.5 | 3.5 to 5.0 |
| Non-volatile ester [5] | 5.0 to 22 | 5.0 to 20 | 5.0 to 15 | 5.0 to 10 |

|  | | | | |
|---|---|---|---|---|
| Volatile silicone compound [7] | 1.0 to 10 | 1.5 to 8.0 | 2.0 to 6.0 | 2.0 to 5.0 |
| Triethyl citrate and/or propylene carbonate | 0.2 to 5.0 | 0.3 to 3.0 | 0.4 to 2.0 | 0.5 to 1.5 |
| Propellant [8] | to make 100 | to make 100 | to make 100 | to make 100 |
|  | AF 149 | AF 150 | AF 151 | AF 152 |
| Aluminum salt of formula (I) [1] | 2.0 to 6.0 | 2.5 to 5.5 | 3.0 to 5.5 | 3.5 to 5.0 |
| Non-volatile ester [5] | 5.0 to 22 | 5.0 to 20 | 5.0 to 15 | 5.0 to 10 |
| Volatile silicone compound [7] | 1.0 to 10 | 1.5 to 8.0 | 2.0 to 6.0 | 2.0 to 5.0 |
| Triethyl citrate and/or propylene carbonate | 0.2 to 5.0 | 0.3 to 3.0 | 0.4 to 2.0 | 0.5 to 1.5 |
| Propellant [8] | to make 100 | to make 100 | to make 100 | to make 100 |
|  | AF 153 | AF 154 | AF 155 | AF 156 |
| Aluminum salt of formula (I) [2] | 2.0 to 6.0 | 2.5 to 5.5 | 3.0 to 5.5 | 3.5 to 5.0 |
| Non-volatile ester [5] | 5.0 to 22 | 5.0 to 20 | 5.0 to 15 | 5.0 to 10 |
| Volatile silicone compound [7] | 1.0 to 10 | 1.5 to 8.0 | 2.0 to 6.0 | 2.0 to 5.0 |
| Triethyl citrate and/or propylene carbonate | 0.2 to 5.0 | 0.3 to 3.0 | 0.4 to 2.0 | 0.5 to 1.5 |
| Propellant [8] | to make 100 | to make 100 | to make 100 | to make 100 |
|  | AF 157 | AF 158 | AF 159 | AF 160 |
| Aluminum salt of formula (Ia) | 2.0 to 6.0 | 2.5 to 5.5 | 3.0 to 5.5 | 3.5 to 5.0 |
| Non-volatile ester [5] | 5.0 to 22 | 5.0 to 20 | 5.0 to 15 | 5.0 to 10 |
| Volatile silicone compound [7] | 1.0 to 10 | 1.5 to 8.0 | 2.0 to 6.0 | 2.0 to 5.0 |
| Triethyl citrate and/or propylene carbonate | 0.2 to 5.0 | 0.3 to 3.0 | 0.4 to 2.0 | 0.5 to 1.5 |
| Propellant [8] | to make 100 | to make 100 | to make 100 | to make 100 |
|  | AF 161 | AF 162 | AF 163 | AF 164 |
| Aluminum salt of formula (Ia) [1] | 2.0 to 6.0 | 2.5 to 5.5 | 3.0 to 5.5 | 3.5 to 5.0 |
| Non-volatile ester [5] | 5.0 to 22 | 5.0 to 20 | 5.0 to 15 | 5.0 to 10 |
| Volatile silicone compound [7] | 1.0 to 10 | 1.5 to 8.0 | 2.0 to 6.0 | 2.0 to 5.0 |
| Triethyl citrate and/or propylene carbonate | 0.2 to 5.0 | 0.3 to 3.0 | 0.4 to 2.0 | 0.5 to 1.5 |
| Propellant [8] | to make 100 | to make 100 | to make 100 | to make 100 |
|  | AF 165 | AF 166 | AF 167 | AF 168 |
| Aluminum salt of formula (Ia) [2] | 2.0 to 6.0 | 2.5 to 5.5 | 3.0 to 5.5 | 3.5 to 5.0 |
| Non-volatile ester [5] | 5.0 to 22 | 5.0 to 20 | 5.0 to 15 | 5.0 to 10 |
| Volatile silicone compound [7] | 1.0 to 10 | 1.5 to 8.0 | 2.0 to 6.0 | 2.0 to 5.0 |
| Triethyl citrate and/or propylene carbonate | 0.2 to 5.0 | 0.3 to 3.0 | 0.4 to 2.0 | 0.5 to 1.5 |
| Propellant [8] | to make 100 | to make 100 | to make 100 | to make 100 |
|  | AF 169 | AF 170 | AF 171 | AF 172 |
| Aluminum salt of formula (I) | 2.0 to 6.0 | 2.5 to 5.5 | 3.0 to 5.5 | 3.5 to 5.0 |
| Non-volatile ester [5] | 5.0 to 22 | 5.0 to 20 | 5.0 to 15 | 5.0 to 10 |
| Volatile silicone compound [7] | 1.0 to 10 | 1.5 to 8.0 | 2.0 to 6.0 | 2.0 to 5.0 |
| Triethyl citrate and/or propylene carbonate | 0.2 to 5.0 | 0.3 to 3.0 | 0.4 to 2.0 | 0.5 to 1.5 |
| Bentonite | 0.1 to 2.0 | 0.2 to 1.5 | 0.3 to 1.0 | 0.4 to 0.8 |
| Propellant [8] | to make 100 | to make 100 | to make 100 | to make 100 |
|  | AF 173 | AF 174 | AF 175 | AF 176 |
| Aluminum salt of formula (I) [1] | 2.0 to 6.0 | 2.5 to 5.5 | 3.0 to 5.5 | 3.5 to 5.0 |
| Non-volatile ester [5] | 5.0 to 22 | 5.0 to 20 | 5.0 to 15 | 5.0 to 10 |
| Volatile silicone compound [7] | 1.0 to 10 | 1.5 to 8.0 | 2.0 to 6.0 | 2.0 to 5.0 |
| Triethyl citrate and/or propylene carbonate | 0.2 to 5.0 | 0.3 to 3.0 | 0.4 to 2.0 | 0.5 to 1.5 |
| Bentonite | 0.1 to 2.0 | 0.2 to 1.5 | 0.3 to 1.0 | 0.4 to 0.8 |
| Propellant [8] | to make 100 | to make 100 | to make 100 | to make 100 |
|  | AF 177 | AF 178 | AF 179 | AF 180 |
| Aluminum salt of formula (I) [2] | 2.0 to 6.0 | 2.5 to 5.5 | 3.0 to 5.5 | 3.5 to 5.0 |
| Non-volatile ester [5] | 5.0 to 22 | 5.0 to 20 | 5.0 to 15 | 5.0 to 10 |
| Volatile silicone compound [7] | 1.0 to 10 | 1.5 to 8.0 | 2.0 to 6.0 | 2.0 to 5.0 |
| Triethyl citrate and/or propylene carbonate | 0.2 to 5.0 | 0.3 to 3.0 | 0.4 to 2.0 | 0.5 to 1.5 |

|  | | | | |
|---|---|---|---|---|
| Bentonite | 0.1 to 2.0 | 0.2 to 1.5 | 0.3 to 1.0 | 0.4 to 0.8 |
| Propellant [8] | to make 100 | to make 100 | to make 100 | to make 100 |
|  | AF 181 | AF 182 | AF 183 | AF 184 |
| Aluminum salt of formula (Ia) | 2.0 to 6.0 | 2.5 to 5.5 | 3.0 to 5.5 | 3.5 to 5.0 |
| Non-volatile ester [5] | 5.0 to 22 | 5.0 to 20 | 5.0 to 15 | 5.0 to 10 |
| Volatile silicone compound [7] | 1.0 to 10 | 1.5 to 8.0 | 2.0 to 6.0 | 2.0 to 5.0 |
| Triethyl citrate and/or propylene carbonate | 0.2 to 5.0 | 0.3 to 3.0 | 0.4 to 2.0 | 0.5 to 1.5 |
| Bentonite | 0.1 to 2.0 | 0.2 to 1.5 | 0.3 to 1.0 | 0.4 to 0.8 |
| Propellant [8] | to make 100 | to make 100 | to make 100 | to make 100 |
|  | AF 185 | AF 186 | AF 187 | AF 188 |
| Aluminum salt of formula (Ia) [1] | 2.0 to 6.0 | 2.5 to 5.5 | 3.0 to 5.5 | 3.5 to 5.0 |
| Non-volatile ester [5] | 5.0 to 22 | 5.0 to 20 | 5.0 to 15 | 5.0 to 10 |
| Volatile silicone compound [7] | 1.0 to 10 | 1.5 to 8.0 | 2.0 to 6.0 | 2.0 to 5.0 |
| Triethyl citrate and/or propylene carbonate | 0.2 to 5.0 | 0.3 to 3.0 | 0.4 to 2.0 | 0.5 to 1.5 |
| Bentonite | 0.1 to 2.0 | 0.2 to 1.5 | 0.3 to 1.0 | 0.4 to 0.8 |
| Propellant [8] | to make 100 | to make 100 | to make 100 | to make 100 |
|  | AF 189 | AF 190 | AF 191 | AF 192 |
| Aluminum salt of formula (Ia) [2] | 2.0 to 6.0 | 2.5 to 5.5 | 3.0 to 5.5 | 3.5 to 5.0 |
| Non-volatile ester [5] | 5.0 to 22 | 5.0 to 20 | 5.0 to 15 | 5.0 to 10 |
| Volatile silicone compound [7] | 1.0 to 10 | 1.5 to 8.0 | 2.0 to 6.0 | 2.0 to 5.0 |
| Triethyl citrate and/or propylene carbonate | 0.2 to 5.0 | 0.3 to 3.0 | 0.4 to 2.0 | 0.5 to 1.5 |
| Bentonite | 0.1 to 2.0 | 0.2 to 1.5 | 0.3 to 1.0 | 0.4 to 0.8 |
| Propellant [8] | to make 100 | to make 100 | to make 100 | to make 100 |

[1] Aluminum salt of formula (I) or (Ia) has an aluminum to chloride ratio of 1.65:1 to 1.88:1;
[2] aluminum salt of formula (I) or (Ia) has an aluminum to chloride ratio of 1.65:1 to 1.88:1, a chloride content of 17 to 20 wt.%, based on the total weight of the respective aluminum salt, and a peak surface area proportion of peak 4 in relation to the total surface area of all peaks in the chromatogram of 40 to 55%, (determined by way of GPC using an Agilent Zorbax PSM 60S column, using 0.02M HCl as the eluent);
[3] non-volatile ester has a refractive index of 1.481 to 1.500;
[4] mixture of a first non-volatile ester (E1) having a $R_f$ of 1.481 to 1,485 and a second non-volatile ester (E2) having a $R_f$ of 1.486 to 1.500 ($R_f$ measured at 20° C. in each case) in a weight ratio of 1:5 to 1:3, wherein the first non-volatile ester (E1) is $C_{12}$ to $C_{15}$ alkyl benzoate and the second non-volatile ester (E2) is phenoxyethyl caprylate;
[5] non-volatile ester is a mixture of $C_{12}$ to $C_{15}$ alkyl benzoate, phenoxyethyl caprylate, ethylhexyl palmitate and isopropyl myristate;
[6] selected from cyclic silicone compounds having 3 to 6 siloxane units, linear silicone compounds having 6 to 10 siloxane units, and the mixtures thereof;
[7] volatile silicone compound is cyclopentasiloxane;
[8] selected from the group consisting of propane, n-butane, iso-butane and the mixtures thereof.

Embodiments AF 1 to 24 and AF 53 to 72 have a weight ratio of the aluminum salt of formula (I) or (Ia) to the non-volatile ester of 1:1.2 to 1:2. Embodiments AF 1 to AF 24 and AF 97 to AF 120 furthermore have a weight ratio of the aluminum salt of formula (I) or (Ia) to the volatile silicone compound of 2.5:1 to 1:1.1.

Due to the use of a combination of aluminum salts of formula (I) or (Ia) with non-volatile esters and volatile silicone compounds, the aforementioned embodiments 1 to 192 of the antiperspirant cosmetic agents according to the invention result in reduced residue build-up, in particular on textiles. Furthermore, the aforementioned combination increases the effectiveness of the aluminum salt of formula (I) or (Ia), so that lower amounts of these salts may be used to achieve an antiperspirant action comparable to the related art without the aforementioned combination. Due to the lower amount of aluminum salts of formula (I) or (Ia), improved cosmetic properties, and in particular an improved dryness sensation on the skin and improved skin tolerability are achieved.

A second subject matter of the present invention is a non-therapeutic cosmetic method for preventing and/or reducing perspiration of the body, in which a cosmetic agent according to the invention is applied to the skin, and in particular to the skin of the axilla region, and remains on the skin for at least 1 hour, especially for at least 2 hours, preferably for at least 4 hours, and in particular for at least 6 hours.

At a reduced amount of active antiperspirant agent (aluminum salt of formula (I) or (Ia)), the method according to the invention, using the cosmetic agents according to the invention in the form of an aerosol, comprising a combination of aluminum salt of formula (I) or (Ia) and at least one non-volatile ester and at least one volatile silicone compound in certain weight ratios, results in a comparable antiperspirant action compared to antiperspirants of the related art that do not comprise the above-described combination. The reduced amount of aluminum salt of formula (I) and/or (Ia), and the combination with the at least one non-volatile ester and the at least one volatile silicone compound, allow the residue build-up to be considerably decreased. In addition, these agents have improved cosmetic properties, and in particular an improved dryness sensation.

What was said above with respect to the cosmetic agents according to the invention applies, mutatis mutandis, with respect to further preferred embodiments of the method according to the invention, and in particular with respect to the cosmetic agents used therein.

Finally, a third subject matter of the present invention is the use of a combination of a) aluminum salts of formula (I) $Al_a(OH)_bCl_c$ (I), where
 a denotes numbers from 1 to 4;
 b denotes numbers from 1 to 4.9, and
 c denotes numbers from 1.5 to 3;
b) at least one non-volatile ester; and
c) at least one volatile silicone compound in propellant-containing cosmetic agents for improving the antiperspirant action, while also reducing residue build-up, in particular on textiles. The aforementioned combination significantly improves the antiperspirant action of propellant-containing cosmetic agents. At the same time, the aforementioned combination can reduce residue build-up, in particular on textiles.

According to the invention, the term "combination" shall be understood to mean a mixture of the three aforementioned compounds a) to c).

Preferred combinations according to the invention have a certain weight ratio of the at least one non-volatile ester to the at least one volatile silicone compound. It is therefore advantageous according to the invention if the weight ratio of the at least one non-volatile ester b) to the at least one volatile silicone compound v) in the combination is 5:1 to 1:1, especially 4:1 to 1:1, preferably 3:1 to 1:1, and in particular 2:1 to 1.2:1. Use of the aforementioned weight ratios of the at least one non-volatile ester to the at least one volatile silicone compound results in reduced residue build-up and an improved dryness sensation. In addition, the antiperspirant action of the aforementioned aluminum salt is not adversely affected.

What was said with respect to the antiperspirant cosmetic agents according to the invention applies, mutatis mutandis, to further embodiments of the use according to the invention, in particular with respect to the used aluminum salt of formula (I) or (Ia), the non-volatile ester, and the volatile silicone compound.

In summary, the present invention is in particular characterized by the following items:

1. An antiperspirant cosmetic agent, comprising, based on the total weight thereof,
 a) 2.5 to 15 wt. % of at least one aluminum salt of formula (I) $Al_a(OH)_bCl_c$ (I), where a denotes numbers from 1 to 4, b denotes numbers from 1 to 4.9, and c denotes numbers from 1.5 to 3;
 b) 5.0 to 25 wt. % of at least one non-volatile ester;
 c) at least one volatile silicone compound; and
 d) at least one propellant,
 wherein the weight ratio of the at least one non-volatile ester b) to the at least one volatile silicone compound c) in the agent is 10:1 to 1:1.5.

2. The antiperspirant cosmetic agent according to item 1, characterized by comprising at least one aluminum salt of formula (Ia) $Al_d(OH)_eCl_f$, where d denotes the number 2, e denotes the number 4.5, and f denotes the number 1.5.

3. The antiperspirant cosmetic agent according to either item 1 or 2, characterized by comprising at least one aluminum salt of formula (I), and in particular of formula (Ia), having a molar ratio of aluminum to chloride of 1.26:1 to 1.90:1, especially 1.35:1 to 1.88:1, preferably 1.40:1 to 1.88:1, and in particular 1.65:1 to 1.88:1.

4. The antiperspirant cosmetic agent according to any one of the preceding items, characterized by comprising at least one aluminum salt of formula (I), and in particular of formula (Ia), having a chloride content of 5 to 35 wt. %, especially 10 to 30 wt. %, preferably 15 to 25 wt. %, and in particular 17 to 20 wt. %, based on the total weight of the aluminum salt of formula (I), and in particular of formula (Ia).

5. The antiperspirant cosmetic agent according to any one of the preceding items, characterized by comprising at least one aluminum salt of formula (I), and in particular of formula (Ia), having a peak surface area proportion of peak 4 to the total surface area of all peaks in the chromatogram of 30 to 80%, especially of 32 to 70%, preferably of 35 to 60%, and in particular of 40 to 55%.

6. The antiperspirant cosmetic agent according to any one of the preceding items, characterized by comprising, based on the total weight thereof, 2.0 to 6.0 wt. %, especially 2.5 to 5.5 wt. %, preferably 3.0 to 5.5 wt. %, and in particular 3.5 to 5.0 wt. % of at least one aluminum salt of formula (I), and in particular of formula (Ia).

7. The antiperspirant cosmetic agent according to any one of the preceding items, characterized by comprising at least one non-volatile ester having a refractive index $R_f$, measured at 20° C., of 1.481 to 1.590, especially of 1.481 to 1.560, preferably of 1.481 to 1.540, and in particular of 1.481 to 1.500.

8. The antiperspirant cosmetic agent according to any one of the preceding items, characterized by comprising at least one first non-volatile ester (E1) having a refractive index $R_f$, measured at 20° C., of 1.481 to 1.485, and at least one second non-volatile ester (E2) having a refractive index $R_f$, measured at 20° C., of 1.486 to 1.500, and in particular $C_{12}$ to $C_{15}$ alkyl benzoate (E1) and phenoxyethyl caprylate (E2), in a weight ratio of E1:E2 of 1:10 to 10:1, especially of 1:8 to 8:1, preferably of 1:6 to 1:1, and in particular of 1:5 to 1:3.

9. The antiperspirant cosmetic agent according to any one of the preceding items, characterized by comprising at least one non-volatile ester from the group consisting of $C_{12}$ to $C_{15}$ alkyl benzoate, phenoxyethyl caprylate, ethylhexyl palmitate, isopropyl myristate and the mixtures thereof, and in particular $C_{12}$ to $C_{15}$ alkyl benzoate and phenoxyethyl caprylate and ethylhexyl palmitate and isopropyl myristate.

10. The antiperspirant cosmetic agent according to any one of the preceding items, characterized by comprising, based on the total weight thereof, 5.0 to 22 wt. %, especially 5.0 to 20 wt. %, preferably 5.0 to 15 wt. %, and in particular 5.0 to 10 wt. % of at least one non-volatile ester, and in particular $C_{12}$ to $C_{15}$ alkyl benzoate and/or phenoxyethyl caprylate and/or ethylhexyl palmitate and/or isopropyl myristate.

11. The antiperspirant cosmetic agent according to any one of the preceding items, characterized by having a weight ratio of the at least one aluminum salt of formula (I), and in particular of formula (Ia), to the at least one non-volatile ester, and in particular $C_{12}$ to $C_{15}$ alkyl benzoate and/or phenoxyethyl caprylate and/or ethylhexyl palmitate and/or isopropyl myristate, of 2:1 to 1:5, especially of 1:1 to 1:4, preferably of 1:1.2 to 1:3, and in particular of 1:1.2 to 1:2.

12. The antiperspirant cosmetic agent according to any one of the preceding items, characterized by comprising at least one volatile silicone compound, selected from the group consisting of cyclic silicone compounds having 2 to 10, and in particular 3 to 6, siloxane units, linear silicone compounds having 2 to 10, and in particular 6 to 10, siloxane units, and the mixtures thereof.

13. The antiperspirant cosmetic agent according to item 12, characterized in that the at least one volatile silicone compound is selected from cyclic silicone compounds having 3 to 6 siloxane units, and in particular cyclopentasiloxane.

14. The antiperspirant cosmetic agent according to any one of the preceding items, characterized by comprising, based on the total weight thereof, 1.0 to 10 wt. %, especially 1.5 to 8.5 wt. %, preferably 2.0 to 6.0 wt. %, and in particular 2.0 to 5.0 wt. % of at least one volatile silicone compound, and in particular cyclopentasiloxane.

15. The antiperspirant cosmetic agent according to any one of the preceding items, characterized by having a weight ratio of the at least one aluminum salt of formula (I), and in particular of formula (Ia), to the at least one volatile silicone compound, and in particular cyclopentasiloxane, of 5:1 to 1:3, especially of 4:1 to 1:2, preferably of 3:1 to 1:1.5, and in particular of 2.5:1 to 1:1.1.

16. The antiperspirant cosmetic agent according to any one of the preceding items, characterized by comprising at least one propellant, selected from the group consisting of propane, propene, n-butane, iso-butane, iso-butene, n-pentane, pentene, iso-pentane, iso-pentene, methane, ethane, dimethyl ether, nitrogen, air, oxygen, nitrous oxide, 1,1,1,3-tetrafluoro ethane, heptafluoro-n-propane, perfluoroethane, mono chloro difluoromethane, 1,1-difluoroethane, tetrafluoropropene, and the mixtures thereof, and in particular propane and/or n-butane and/or iso-butane.

17. The antiperspirant cosmetic agent according to any one of the preceding items, characterized by comprising, based on the total weight thereof, 20 to 80 wt. %, especially 55 to 80 wt. %, preferably 60 to 80 wt. %, and in particular 65 to 80 wt. % of at least one propellant, and in particular propane and/or n-butane and/or iso-butane.

18. The antiperspirant cosmetic agent according to any one of the preceding items, characterized by having a weight ratio of the at least one volatile ester b) to the at least one volatile silicone compound c) of 5:1 to 1:1, especially of 4:1 to 1:1, preferably of 3:1 to 1:1, and in particular of 2:1 to 1.2:1.

19. The antiperspirant cosmetic agent according to any one of the preceding items, characterized by additionally comprising, based on the total weight thereof, 0.05 to 5.0 wt. %, especially 0.1 to 3.0 wt. %, preferably 0.15 to 2.0 wt. %, and in particular 0.2 to 1.5 wt. % triethyl citrate and/or propylene carbonate.

20. The antiperspirant cosmetic agent according to any one of the preceding items, characterized by additionally comprising, based on the total weight thereof, 0.1 to 2.0 wt. %, especially 0.2 to 1.5 wt. %, preferably 0.3 to 1.0 wt. %, and in particular 0.4 to 0.8 wt. % bentonite.

21. The antiperspirant cosmetic agent according to any one of the preceding items, characterized by being anhydrous.

22. The antiperspirant cosmetic agent according to any one of the preceding items, characterized by comprising no alkoxylated, and in particular no ethoxylated and/or propoxylated, silicones.

23. A non-therapeutic cosmetic method for preventing and/or reducing perspiration of the body, in which a cosmetic agent according to any one of items 1 to 22 is applied to the skin, and in particular to the skin of the axilla region, and remains on the skin for at least 1 hour, especially for at least 2 hours, preferably for at least 4 hours, and in particular for at least 6 hours.

24. Use of a combination of
a) aluminum salts of formula $$Al_a(OH)_bCl_c \qquad (I),$$

where a denotes numbers from 1 to 4, b denotes numbers from 1 to 4.9, and c denotes numbers from 1.5 to 3;

b) at least one non-volatile ester; and c) at least one volatile silicone compound in propellant-containing cosmetic agents for improving the antiperspirant action, while also reducing residue build-up, in particular on textiles.

25. Use according to item 24, characterized in that the weight ratio of the at least one volatile ester b) to the at least one volatile silicone compound d) in the combination is 5:1 to 1:1, especially 4:1 to 1:1, preferably 3:1 to 1:1, and in particular 2:1 to 1.2:1.

The following examples describe the present invention in more detail, without limiting it to these examples.

EXAMPLES

The aluminum salt used in the following examples is preferably an aluminum salt of formula (Ia) having a molar ratio of aluminum to chloride of 1.65:1 to 1.88:1, a chloride content of 17 to 20 wt. %, based on the total weight of the aluminum salt of formula (Ia), and a peak 4 surface area proportion of 40 to 55%, (measured by way of GPC using an Agilent Zorbax PSM 60S column, using 0.02 M HCl as the eluent). The non-volatile ester is preferably a mixture of $C_{12}$ to $C_{15}$ alkyl benzoate, phenoxyethyl caprylate, ethylhexyl palmitate and isopropyl myristate. The volatile silicone compound used is preferably cyclopentasiloxane. The propellant is preferably a mixture of propane and n-butane in a weight ratio of 15:85. The following quantity information is indicated in wt. %, based on the respective total weight of the cosmetic agent according to the invention.

| Raw material | E1 | E2 | V1 | V2 |
| --- | --- | --- | --- | --- |
| Aluminum salt of formula (I) | 3.5 | 4.9 | — | — |
| Activated aluminum(III) chloride (AACH 71, Summit Reheis) | — | — | 3.5 | 4.9 |
| Non-volatile ester | 6.6 | 6.6 | 6.6 | 6.6 |
| Volatile silicone compound | 3.7 | 2.3 | 3.7 | 2.3 |
| Triethyl citrate | 0.60 | 0.60 | 0.60 | 0.60 |
| Bentone 38 V CG | 0.38 | 0.38 | 0.38 | 0.38 |
| Propylene carbonate | 0.14 | 0.14 | 0.14 | 0.14 |
| Perfume | 0.75 | 0.75 | 0.75 | 0.75 |
| Propellant | to make 100 | to make 100 | to make 100 | to make 100 |

To prepare the antiperspirant cosmetic agents according to the invention, all ingredients, with the exception of the propellant, are mixed and filled into aerosol cans. These are subsequently supplied with the appropriate amount of propellant. Thereafter, after spraying for 2 seconds onto black cardboard, the residue index (white) was determined by a visual comparison to a reference scale (0=no residue, 4=a lot of residue), wherein three determinations were carried out for each spray. In addition, the relative dryness sensation was ascertained after 3 days of application in a hemilateral comparison. The values obtained are provided in the table below:

| Parameter | E1 | E2 | V1 | V2 |
|---|---|---|---|---|
| Residue index (white) | 0.5 | 1.0 | 1.0 | 1.5 |
| Relative dryness sensation | Better than V1 | Better than V2 | Worse than E1 | Worse than E2 |

Compared to the use of aluminum chlorohydrate (V1 and V2), the use of a combination according to the invention composed of a specific aluminum salt, at least one non-volatile ester, and at least one volatile silicone compound (E1 and E2) results in reduced residue (lower residue index) and an improved dryness sensation.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An antiperspirant cosmetic agent, comprising, based on the total weight thereof,
    a) 2.5 to 15 wt. % of at least one aluminum salt of formula (I) $Al_a(OH)_bCl_c$(I),
    where
    a denotes numbers from 1 to 4;
    b denotes numbers from 1 to 4.9, and
    c denotes numbers from 1.5 to 3 and wherein the at least one aluminum salt of formula (I) has a molar ratio of aluminum to chloride of 1.26:1 to 1.90:1;
    b) 3 to 15 wt. % of non-volatile esters;
    c) at least one volatile silicone compound; and
    d) at least one propellant,
    wherein the weight ratio of the non-volatile esters b) to the at least one
    volatile silicone compound c) in the agent is 10:1 to 1:1.5, and
    wherein the non-volatile esters are a mixture of $C_{12}$ to $C_{15}$ alkyl benzoate, phenoxyethyl caprylate, ethylhexyl palmitate, and isopropyl myristate.

2. The antiperspirant cosmetic agent according to claim 1, wherein the at least one formula (I) is the at least one aluminum salt of formula (Ia) $Al_a(OH)_bCl_c$, where a denotes the number 2, b denotes the number 4.5, and c denotes the number 1.5.

3. The antiperspirant cosmetic agent according to claim 1, wherein the at least one aluminum salt of formula (I) has a molar ratio of aluminum to chloride of 1.40:1 to 1.88:1.

4. The antiperspirant cosmetic agent according to claim 1, wherein the at least one aluminum salt of formula (I) has a molar ratio of aluminum to chloride of 1.65:1 to 1.88:1.

5. The antiperspirant cosmetic agent according to claim 1, wherein the at least one aluminum salt of formula (I) comprises 2.0 to 6.0 wt. % of the cosmetic agent.

6. The antiperspirant cosmetic agent according to claim 1, wherein the at least one aluminum salt of formula (I) comprises 2.5 to 5.5 wt. % of the cosmetic agent.

7. The antiperspirant cosmetic agent according to claim 1, wherein the at least one aluminum salt of formula (I) comprises 3.5 to 5.0 wt. % of the cosmetic agent.

8. The antiperspirant cosmetic agent according to claim 1, wherein the non-volatile ester comprises, based on the total weight thereof, 5.0 to 15 wt. % of the cosmetic agent.

9. The antiperspirant cosmetic agent according to claim 1, wherein the at least one propellant comprises, based on the total weight of the cosmetic agent, 20-80%.

10. The antiperspirant cosmetic agent according to claim 1, wherein the at least one propellant includes propane and/or n-butane and/or iso-butane.

11. The antiperspirant cosmetic agent according to claim 1, wherein the weight ratio of the non-volatile esters b) to the at least one volatile silicone compound c) is 5:1 to 1:1.

12. The antiperspirant cosmetic agent according to claim 1, wherein the weight ratio of the non-volatile esters b) to the at least one volatile silicone compound c) is 4:1 to 1:1.

13. The antiperspirant cosmetic agent according to claim 1, wherein the weight ratio of the non-volatile esters b) to the at least one volatile silicone compound c) is 3:1 to 1:1.

14. The antiperspirant cosmetic agent according to claim 1, wherein the weight ratio of the non-volatile esters b) to the at least one volatile silicone compound c) is 2:1 to 1.2:1.

15. A non-therapeutic cosmetic method for preventing and/or reducing perspiration of the body, in which a cosmetic agent according to claim 1 is applied to the skin and remains on the skin for at least 1 hour.

* * * * *